United States Patent
Miles

[11] Patent Number: 5,916,199
[45] Date of Patent: Jun. 29, 1999

[54] TAPELESS TUBING ANCHORING SYSTEM WITH INTRAVENOUS APPLICATIONS

[76] Inventor: John E. Miles, 112 N. Washington, Fleming, Colo. 80728

[21] Appl. No.: 08/889,543

[22] Filed: Jul. 8, 1997

Related U.S. Application Data

[60] Provisional application No. 60/021,596, Jul. 11, 1996.

[51] Int. Cl.⁶ ........................................ A61M 5/00
[52] U.S. Cl. ............................................... 604/174
[58] Field of Search .................... 604/174, 179, 604/180

[56] References Cited

U.S. PATENT DOCUMENTS

| | | |
|---|---|---|
| 3,765,421 | 10/1973 | Poprik . |
| 3,812,851 | 5/1974 | Rodriguez . |
| 3,878,849 | 4/1975 | Muller et al. . |
| 4,088,316 | 5/1978 | Szafianski . |
| 4,316,461 | 2/1982 | Marais et al. . |
| 4,416,664 | 11/1983 | Womack . |
| 4,453,933 | 6/1984 | Speaker . |
| 4,499,975 | 2/1985 | Tsuji . |
| 4,585,443 | 4/1986 | Kaufman . |
| 4,662,873 | 5/1987 | Lash et al. . |
| 4,666,434 | 5/1987 | Kaufman . |
| 4,671,787 | 6/1987 | Widman . |
| 4,772,264 | 9/1988 | Cragg . |
| 4,846,807 | 7/1989 | Safadago . |
| 4,955,864 | 9/1990 | Hajduch . |
| 4,966,589 | 10/1990 | Kaufman . |
| 5,084,026 | 1/1992 | Shapiro . |
| 5,279,574 | 1/1994 | Forren . |
| 5,342,317 | 8/1994 | Claywell . |
| 5,346,479 | 9/1994 | Schneider . |

*Primary Examiner*—John D. Yasko
*Attorney, Agent, or Firm*—Workman, Nydegger & Seeley

[57] ABSTRACT

A tapeless anchoring system comprising a first holder and a second holder. The first holder comprises a base and a cover. The base has a top surface and a bottom surface. The top surface of the base has a channel configured to receive a portion of tubing. The cover is securable to the top surface of the base. The cover has a top surface and a bottom surface with a first recess formed therein configured to cooperate with the channel to form a passageway that is configured to removably enclose a portion of the tubing. The second holder comprises a bottom portion and a top portion. The bottom that has an interior surface and an exterior surface. The interior surface of the bottom portion has a channel formed therein. The top portion is securable to the interior surface of the bottom portion. The top portion has an exterior surface and an interior surface with a recess formed therein. The channel and the recess are configured to cooperate to form an elongated hole configured to removably receive a portion of the tubing. A first elongated strap and a second elongated strap are connected to the first holder and the second holder, respectively, and are configured to be wrapped around the limb of the patient to selectively, nondestructively secure the first and the second holder in place on the patient without direct adhesion to the skin of the patient.

37 Claims, 4 Drawing Sheets

TAPELESS TUBING ANCHORING SYSTEM WITH INTRAVENOUS APPLICATIONS

BACKGROUND OF THE INVENTION

1. Related Applications

Benefit of the earlier filing date of a Provisional Patent Application Ser. No. 60/021,596, filed Jul. 11, 1996, is claimed for this application under 35 U.S.C. §119(e).

2. The Field of the Invention

This invention relates to devices for holding tubing, and more particularly to an apparatus for holding tubing such as intravenous tubing utilized in the field of medicine for the intravenous injection of liquids.

3. Present State of the Art

In a wide variety of medical treatment situations it is necessary and/or standard practice to use intravenous instruments, such as a needle or catheter, for the proper administration of fluids, medication, electrolytes, and the like, or an analogous purpose such as blood transfusions. The most convenient location for the placement of the intravenous device is in a vein in the hand or arm, do to the fact that the veins in these areas are relatively large and close to the skin and are easily located by medical personnel.

When an intravenous instrument is used and is attached to the end of the tubing in giving intravenous medication, blood plasma, anesthesia and the like, the tubing tends to displace the intravenous instrument because of its weight and interferes with the proper operation of the apparatus. As a result, after the intravenous instrument is inserted into the vein and connected to the tubing, the tubing is typically taped to the limb of the patient to secure the tubing and to maintain proper orientation and reduce displacement or even to prevent the accidental removal of the intravenous instrument from the vein. Adhesive tape is used to prevent the needle or catheter and the tubing from decoupling, twisting, or pulling out of the vein as well as any interference with the flow of fluid through the tubing.

Adhesive tape is difficult to remove from the patient without causing discomfort. When the adhesive tape is removed, any hair growing upon the limb may be inadvertently removed. In addition, there are patients who either have or develop allergies to the adhesive on the tape or possess sensitive skin that is damaged by tape removal. The use of adhesive tape also results in pressure upon the base of the needle or catheter and the tubing and causes them to press into the flesh of the patient. The pressure from the end of an intravenous instrument needle and the tubing pressing on the skin not only is uncomfortable, but in some cases bruises the flesh.

An additional concern is that the use of the adhesive tape over a lengthy period of time can cause tissue breakdown and other injuries to the soft tissue of the area as well as to the nerve network and various vessels in the skin. Some patients, particularly those who are elderly, have fragile skin that is easily damaged by adhesive tape.

In addition, there are many incidents where the adhesive tape applied to the flexible tubing is ineffective in protecting the intravenous installation. Many patients inadvertently move in a manner which applies tension to the tubing and pulls the needle or catheter from the insertion site or displaces the needle or catheter. At the same time, other individuals nearby may accidentally engage or snag the tubing and cause tension on it. Tape is particularly ineffective for difficult patients who may try to tear or peel off the tape and remove the tubing and intravenous device.

Today many hospitals are encouraging patients to exercise, even while intravenous tubing is in place, by having the patient carry the intravenous fluid supply container while walking. This practice further increases the opportunity for the tubing to become caught on nearby objects, resulting in the accidental removal of the intravenous needle or catheter. When the intravenous catheter or needle is accidentally removed, it is frequently the case that the vein insertion point is lacerated slightly requiring that a new insertion point be used. The number of convenient vein locations which are suitable for catheter insertion is limited, and trauma to these locations may be injurious to the health of a frail patient or at least extremely uncomfortable.

The use of adhesive tape may also lead to functional problems resulting from inexperienced personnel doing the taping or the gradual loosening of the tape due to patient movement or sweating which may cause the tape to loose its grip and fail in its function to maintain the needle, flow tube, and coupling assembly suitably anchored. It is also difficult to apply adhesive to a patient in a moving vehicle such as an ambulance. Finally, using adhesive tape to properly secure the tubing and intravenous instruments takes some time, usually in range of two to three minutes. In an emergency, this may be too long.

There are various devices which have made an attempt to stabilize the intravenous apparatus. The devices have either been very complicated, requiring new intravenous apparatus designs, or have incorporated clips to frictionally hold the tubing in place. Clips that frictionally hold the tubing in place tend to place a compressive force on the tubing which reduces the flow through the tubing.

Some of the devices available include bracelets or strap-like devices in which the flexible tubing is inserted. These devices, however, require the tubing to be in an aperture, which presses down on the tubing, or be strapped into a bracelet. In either case, compression is being placed on the tubing, thereby reducing the flow at that particular section of the tubing.

In most intravenous tubing situations, there is a loop to change directions from exiting the intravenous instrument to heading proximally up the limb of the patient towards the fluid supply. It is very important that the loop not be occluded or compressed, which would interrupt the supply of fluid. In the prior devices, however, the loop of tubing is unprotected and increases the probability that the loop will become entangled as the patient is moving around and will inadvertently dislodge the intravenous device.

SUMMARY AND OBJECTS OF THE INVENTION

It is, therefore, an object of the present invention to provide a tapeless anchoring system capable of securely holding tubing used in medical procedures in place on a patient.

It is a further object of the present invention to prevent decreased fluid flow through the tubing and to prevent the entanglement of the tubing.

Another object of the present invention is to provide a tapeless anchoring system capable of securely holding flexible tubing in place on the patient without causing damage or abrasions to the skin or soft tissue of the patient, pulling the hair of the patient, or otherwise injuring the patient.

Another object of the present invention is to provide a tapeless anchoring system capable of protecting the intravenous tubing formed into a loop as the tubing extends distally from an intravenous device and is redirected proximally up the limb of the patient.

Another object of the present invention is to provide a tapeless anchoring system capable of being quickly assembled and positioned on the patient.

A further object of the present invention is to provide a tapeless anchoring system capable of preventing accidental removal of an intravenous needle or catheter, as well as holding the intravenous tubing in place.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a tapeless anchoring system is provided that includes a first holder and a second holder. The first holder has a passageway formed therein configured to removably enclose a portion of the hollow tubing. The first holder comprises a base and a cover. The base has a bottom surface and a top surface with a channel formed therein configured to receive a portion of the tubing. The cover is securable to the top surface of the base. The cover has a top surface and a bottom surface with a first recess formed therein configured to cooperate with the channel to form a passageway.

The second holder has an elongated hole formed therein configured to removably receive a portion of the tubing. The second holder comprises a bottom portion and a top portion. The bottom portion has an exterior surface and an interior surface with a channel formed therein The top portion has an exterior surface and an interior surface with a recess formed therein configured to cooperate with the channel in the interior surface of the bottom portion to form the elongated hole. The interior surface of the top portion is securable to the interior surface of the bottom portion.

The tapeless anchoring system further includes a first elongated strap connected to the first holder and a second elongated strap removably connected to the second holder. The first elongated strap and the second elongated strap are configured to be wrapped around the limb of the patient to selectively, nondestructively secure the first and the second holder in place on the patient without direct adhesion to the skin of the patient.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof, which are illustrated in the appended drawings. Understanding that these drawings depict only typical embodiments of the invention and are not, therefore, to be considered to be limiting of its scope, the invention will be described and explained with additional specificity and detail through the use of the accompanying drawings in which.

DETAILED DESCRIPTION OF THE PREFERRED EMBODIMENTS

Figure 1:
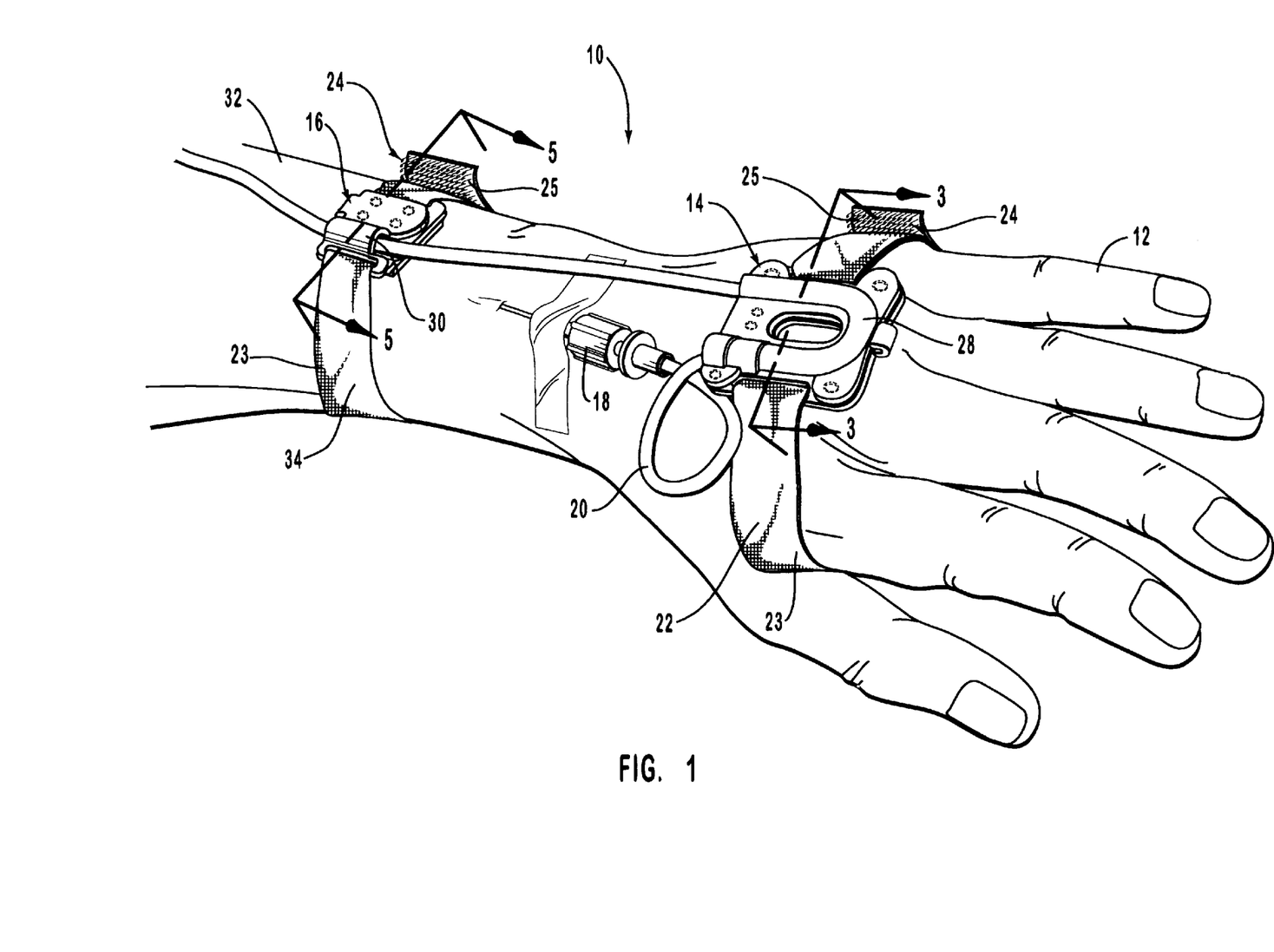
FIG. 1 is a perspective view of one embodiment of the present invention attached to the hand and forearm of the patient.

The present invention relates to a tapeless anchoring system for securing tubing to the limb of a patient. FIG. 1 illustrates one embodiment of the present invention utilized to secure an intravenous needle and flexible intravenous tubing that is attached to the needle to the arm of a patient. It can be appreciated that the tapeless anchoring system 10 shown in FIG. 1 can be utilized with other intravenous systems such as catheters and the like. It should also be appreciated that this system will work as equally well on other limbs of the patient such as a leg of the patient.

One embodiment of tapeless anchoring system 10 is illustrated in FIG. 1. Tapeless anchoring system 10 comprises a first holder 14 and a second holder 16. First holder 14 is attached to the patient proximate to a skin penetrating instrument 18, such as an intravenous needle or catheter. Flexible hollow tubing 20 is attached to intravenous needle 18. According to the usual procedure, flexible tubing 20 is provided with some slack to accommodate movement of the limb of the patient and then is formed into a loop so that flexible tubing 20 can be routed proximally up the limb, such as arm 32, of the patient toward the fluid supply container. The loop that is formed with the flexible tubing 20 is curved and usually has a substantially curvealinear configuration. Other types of hollow tubing may be used. In stead of being flexible, the tubing may be by way of example and without limitation, less flexible but be preformed into the desired configuration.

According to one aspect of the present invention, flexible tubing 20 is enclosed within first holder 14 to protect flexible tubing 20 from being distorted, totally or partially occluded, or becoming entangled while the patient is moving around. One embodiment of first holder 14 is illustrated in FIG. 1. The loop of flexible tubing 20 is completely enclosed within a passageway 28 formed in first holder 14. Passageway 28 is configured to cooperate with flexible tubing 20 and to removably receive flexible tubing 20 within passageway 28 without exerting compressive force on flexible tubing 20 and without reducing the flow of fluid through flexible tubing 20. Passageway 28 may have various configurations as long as passageway 28 is capable of cooperating with tubing 20. It can be appreciated that various types and sizes of hollow tubing 20 may be used with first holder 14 including those that are not flexible. Therefore, passageway 28 is to be configured to cooperate with whatever configuration tubing 20 may have.

As shown in FIG. 1, in one embodiment of first holder 14 passageway 28 is curved. First holder 14 is anchored on the limb of the patient, in this case proximate to a hand 12 of the patient, by a first elongated strap 22. First elongated strap 22 is attached to first holder 14 to securely anchor first holder 14 to the patient without the use of adhesive tape. First elongated strap 22 has a hook-and-pile fastener 24 attached to at least one end for selectively, nondestructively securing first holder 14 in place on the limb of the patient.

First elongated strap 22 comprises a padded material that is placed proximate to the skin of the patient to increase the comfort of the patient. First elongated strap 22 has a pile portion 23 of hook-and-pile fastener 24 extending along the length of first elongated strap 22 on the surface opposite from the skin of the patient. The hook portion 25 of hook-and-pile fastener 24 is located at one end of first elongated strap 22. It can be appreciated that other arrangements of hook-and-pile fastener 24 are equally effective in carrying out the intended function thereof. For example, pile portion 23 may extend only over a portion of first elongated strap 22 or the positions of pile portion 23 and hook portion 25 may be reversed without effecting the function thereof. Hook-and-pile fastener 24 is an example of one possible embodiment of a structure capable of performing the function of fastening means for selectively, nondestructively fixing first elongated strap 22 and first holder 14 in place around the limb of the patient. Other possible types of fastening means for nondestructively selectively fixing first elongated strap 22 in place around the limb of the patient include, by way of example and without limitation, snaps, clasps, hook and eye fasteners, and even belt-like fasteners.

In the embodiment illustrated in FIG. 1, first elongated strap 22 is removably attached to first holder 14. In one alternative embodiment, first elongated strap 22 can be fixedly attached to first holder 14 without effecting the function thereof. First elongated strap 22 is one possible embodiment of a structure capable of performing the function of a first attaching means for securing first holder 14 in place on the limb of the patient. Other embodiments of a first attaching means include elongated ties that can actually be tied around the limb of the patient.

Tapeless anchoring system 10 may also include a second holder 16 at a location on the limb, such as arm 32, of the patient remote from first holder 14. Second holder 16 has an elongated hole 30 to removably receive a portion of flexible tubing 20. Second holder 16 is attached to arm 32 of the patient by a second elongated strap 34. Second elongated strap 34 is removably attached to second holder 16 and encircles arm 32 of the patient to anchor second holder 16 in place without the use of adhesive tape.

Like first elongated strap 22, second elongated strap 34 consists of a padded material that is against the skin of the patient. On the opposite surface of second elongated strap 34 of the padded material is a hook-and-pile fastener 24 for selectively, nondestructively fixing second elongated strap 34 in place around arm 32 of the patient. Second elongated strap 34 is one possible embodiment of a structure performing a function of a second attaching means for securing second holder 16 in place on arm 32 of patient. Other embodiments of a second attaching means include elongated ties that can actually be tied around the limb of the patient.

Hook-and-pile fastener 24 on second elongated strap 34 is the same as that on first elongated strap 22 and the discussion relative to hook-and-pile fastener 24 on first elongated strap 22 is equally applicable to second elongated strap 34. Hook-and-pile fastener 24 is one possible embodiment of structure capable of performing a fastening means on second elongated strap 34. Other possible types of fastening means for nondestructively selectively fixing second elongated strap 34 in place around the limb of the patient include, by way of example and without limitation, snaps, clasps, hook and eye fasteners, and even belt-like fasteners.

Figure 2:
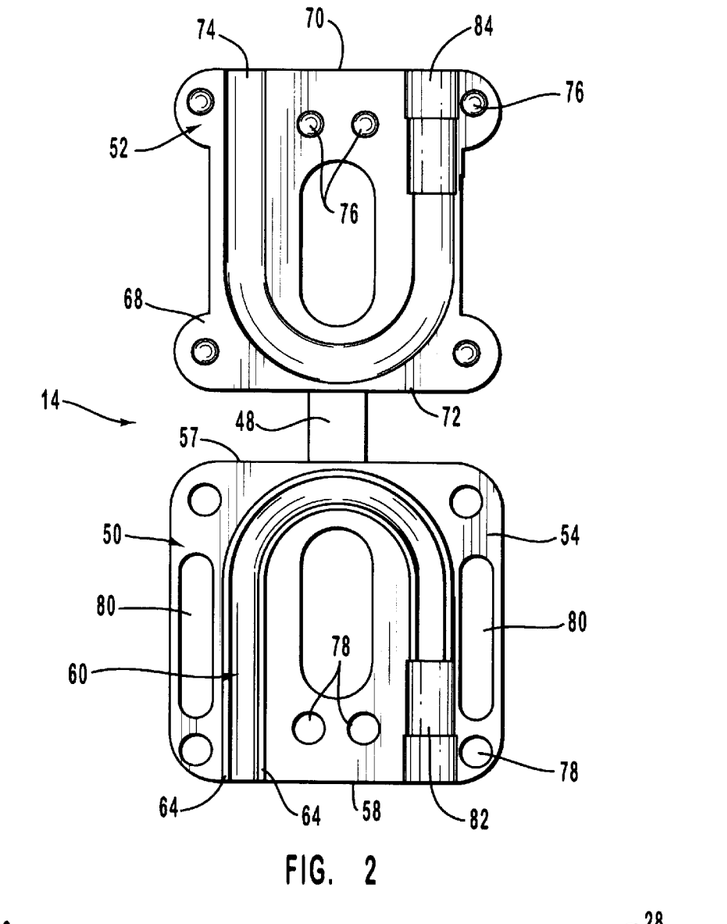
FIG. 2 is a top elevation view of the first holder illustrated in FIG. 1 as unassembled.

FIG. 2 illustrates one embodiment of first holder 14 as unassembled prior to receiving and enclosing flexible hollow tubing 20. First holder 14 comprises a base 50 and a cover 52. Base 50 is hingedly connected to cover 52 by flexible resilient hinge 48. Other methods of connecting base 50 and cover 52 are equally effective in carrying the intended function thereof. Base 50 and cover 52 could be configured by way of example and not limitation, a string-like member, or have a continuous flexible hinge along an entire edge making base 50 and cover 52 more of a one piece unit In addition, other locations for hinge 48 to attach base 50 and cover 52 work equally as well. It can be appreciated that base 50 and cover 52 are not required to be connected at all. Base 50 and cover 52 could be two separate independent pieces and perform the function thereof equally effectively. In the preferred embodiment, base 50 is hingedly attached to cover 52 for ease in assembly as well as manufacturing.

Figure 3:
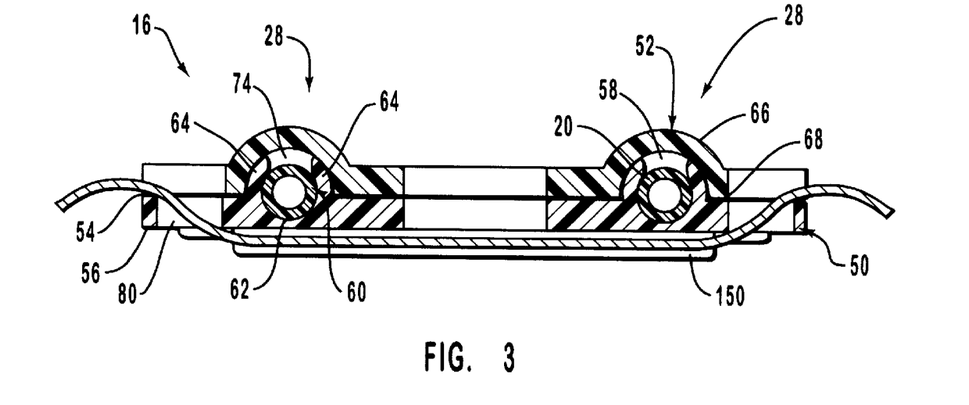
FIG. 3 is a partial cross-sectional elevation view taken along section line 3—3 in FIG. 1.

As shown in FIGS. 2 and 3, base 50 has a top surface 54 and a bottom surface 56. Base 50 also has a proximal side 58 and a distal side 57. A channel 60 is formed in top surface 54 of base 50 that is configured to receive flexible tubing 20. Channel 60 is configured to receive flexible tubing 20 without either exerting compressive force on flexible tubing 20 or without reducing the flow of fluid through flexible tubing 20 while flexible tubing 20 is disposed therein. Channel 60 is curved to receive the loop of flexible tubing 20. Preferably, channel 60 is curved into a substantially curvealinear configuration such as a partial loop in a plane that is parallel with top surface 54 of base 50. Enclosing the loop of flexible tubing 20 within first holder 14 prevents flexible tubing 20 from being pinched to partially or totally restrict the flow of fluid through flexible tubing 20 or from becoming entangled while the patient moves around.

As shown in FIG. 3, cover 52 is selectively securable to top surface 54 of base 50. Cover 52 has a top surface 66 and a bottom surface 68. Cover 52 also has a proximal side 70 and a distal side 72. Bottom surface 68 of cover 52 has a recess 74 configured to cooperate with channel 60 in top surface 54 of base 50 to form passageway 28 in first holder 14. Recess 74 has a curvealinear curved configuration in a plane parallel to top surface 54 of base 50 to cooperate with the configuration of channel 60. Preferably, recess 74 substantially forms a partial loop shape in a plane parallel with top surface 54 of base 50. The open end of the partial loop formed by recess 74 is located at proximal end 70 of cover 52. Correspondingly, the open end of the partial loop shape formed by channel 60 in a plane parallel with top surface 54 of base 50 is at proximal side 58 of base 50.

Other configurations or shapes of passageway 28 in a plane parallel with top surface 54 of base 50 formed by recess 74 and channel 60 are equally effective in carrying out the intended function thereof. Passageway 28 could by way of example and not limitation be curved into any configuration or even be linear depending on the configuration of the tubing. The important feature of passageway 28 is that it be have a configuration in a plane parallel with the top surface 54 of base 50 that conforms with and is capable of cooperating with the configuration of tubing 20.

Channel 60 formed in top surface 54 of base 50 comprises a recess 62 formed in top surface 54 of base 50 and a pair of flexible, substantially upwardly extending walls 64 projecting substantially upward from top surface 54 of base 50. The pair of substantially upwardly extending walls 64 have a spaced apart relationship and recess 62 is located between substantially upwardly extending walls 64.

Figure 3A:
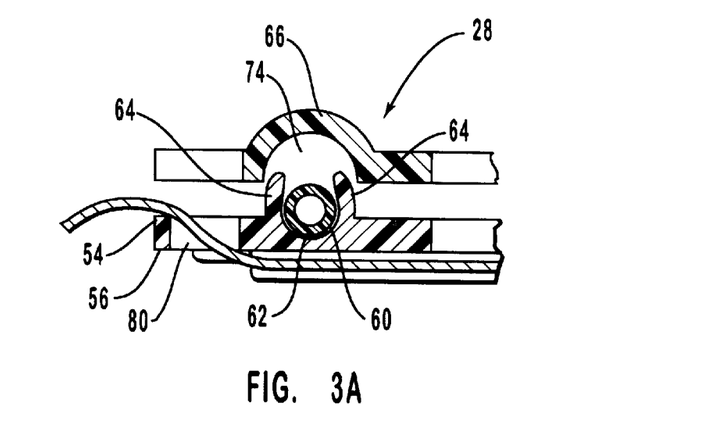
FIG. 3A is a partial cross-sectional elevation view of the channel in first holder prior to being assembled.

As shown in FIG. 3A, the cross-section of channel 60, in a plane substantially perpendicular to top surface 54 of base 50, is configured to receive tubing 20. Channel 60 is configured to compliment the size and shapes of various tubing used in medical procedures. Channel 60 is conformable to flexible tubing 20 without exerting compression on flexible tubing 20 when cover 52 is removably secured to base 50. The cross-section of channel 60 in a plane substantially perpendicular to top surface 54 of base 50, illustrated in FIG. 3A, is preferably substantially U-shaped or configured to complement the shape of tubing 20 that is to be received in channel 60. Preferably, the pair of resilient substantially upwardly extending walls 64 are spaced far enough apart that flexible tubing 20 can be disposed in channel 60 without substantially upwardly extending walls 64 exerting compressive forces on flexible tubing 20 when flexible tubing 20 is disposed in channel 60.

The pair of substantially upwardly extending walls 64 have a varying wall thickness to assist channel 60 with recess 74 in cover 52 to form passageway 28. FIG. 3A illustrates channel 60 prior to cover 52 being removably secured to top surface 54 of base 50. As shown in FIG. 3, when cover 52 is removably secured to base 50, the pair of resilient substantially upwardly extending walls 64 flex slightly to conform to recess 74 formed in bottom surface 68 of cover 52 without compressing flexible tubing 20.

In an alternate embodiment of channel 60, the pair of substantially upwardly extending walls 64 are upright or substantially perpendicular to top surface 54 of base 50. In this embodiment, channel 60 would still have a substantially U-shaped cross-section in a direction perpendicular to top surface 54 of base 50.

Top surface 54 of base 50 is selectively secured to bottom surface 68 of cover 52 by male connectors 76 and female connectors 78 as illustrated in FIG. 2. Male connectors 76 extend outwardly from bottom surface 68 of cover 52. Female connectors 78 are formed in base 50 to cooperate with male connectors 72 for selectively connecting cover 52 to base 50 of first holder 14.

In one embodiment illustrated in FIG. 2, male connectors 76 are formed on cover 52 and female connectors 78 are formed in base 50. Male connectors 76 could be formed on base 50 while female connectors 78 could be formed in cover 52 and perform the function thereof equally as well. Male connectors 76 and female connectors 78 are one possible embodiment of structure capable of performing the function of a first closing means for selectively, nondestructively connecting top surface 54 of base 50 to bottom surface 68 of cover 52. By way of example and not limitation, other configurations of closing means include cover 52 that is configured to snap fit over base 50 or a male member that can be press fit or snap fit into a recess configured to releasably cooperate with the male member.

In one embodiment of the present invention, male connectors 76 are substantially mushroom shaped. The remote end of each male connector 76 is slightly oversized as compared to female connector 78. The remote end of male connector 76 is forced through female connector 76. The proximal end of male connector 76 remains disposed in female connector 78. The oversized remote end of male connector 76 makes it more difficult to accidentally separate base 50 and cover 52 of first holder 14.

As shown in FIG. 2, base 50 of first holder 14 has a pair of elongated apertures 80 for receiving first elongated strap 22. In the embodiment of first holder 14 illustrated in FIGS. 1–3, first elongated strap 22 is removably connected to first holder 14 through elongated apertures 80 formed in base 50. First elongated strap 22 may be fixedly attached to first holder 14 and perform the intended function of such first attaching means for securing first holder 14 in place on the patient equally effectively.

As shown in FIG. 2, one embodiment of first holder 14 may, on one side of channel 60 that substantially forms the open end of channel 60 in a plane that is parallel with top surface 54 of base 50, have an enlarged recess 82 at proximal side 58 of base 50. Correspondingly, recess 74 formed in bottom surface 68 of cover 52 similarly has an enlarged recess 84 at proximal side 70 of cover 52. Recess 82 and recess 84 define an enlarged portion of passageway 28 configured to receive a connector (not shown) that is attached to flexible tubing 20. Enlarged recesses 82 and 84 are optional, and first holder 14 functions equally effectively without recesses 82 and 84.

First holder 14 is an example of a structure capable of performing the function of a first holding means for anchoring flexible hollow tubing in a substantially fixed position on a patient.

Figure 2A:
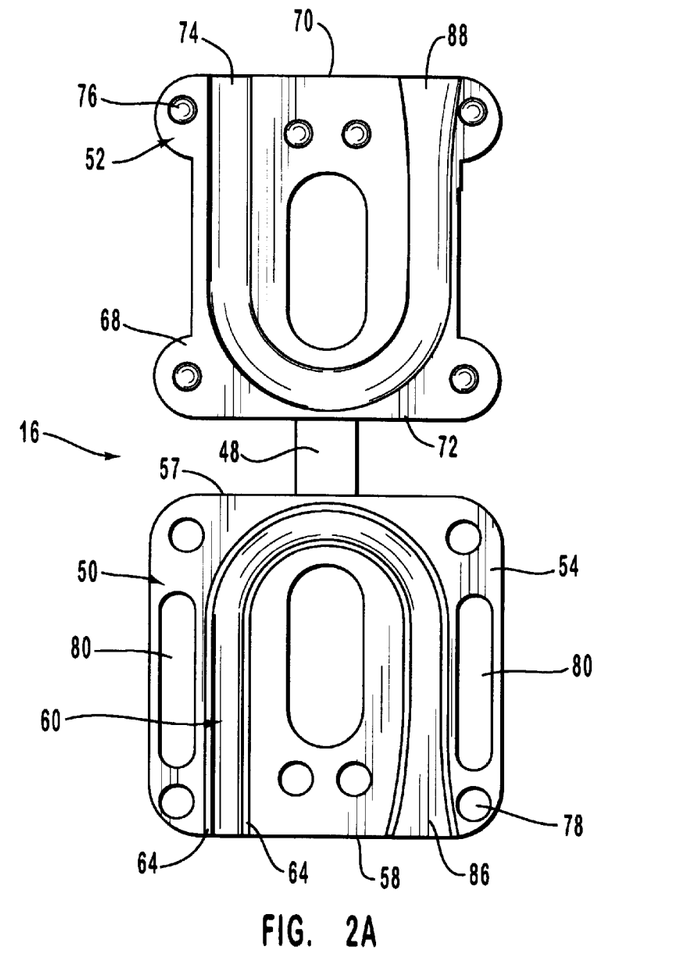
FIG. 2A is a top elevation view of a second embodiment of the first holder as unassembled.

A second embodiment of first holder 14 is shown in FIG. 2A where channel 60 has a flared portion 86 at one side of the open end at the proximal side 58 of base 50. Recess 74 formed in cover 52 has a similar flared portion 88 at proximal side 70 of cover 52. Flared portions 86 and 88 of channel 60 and recess 74, respectively, define an enlarged portion of passageway 28 configured to receive a connector (not shown) that is attached to flexible tubing 20.

Figure 4:
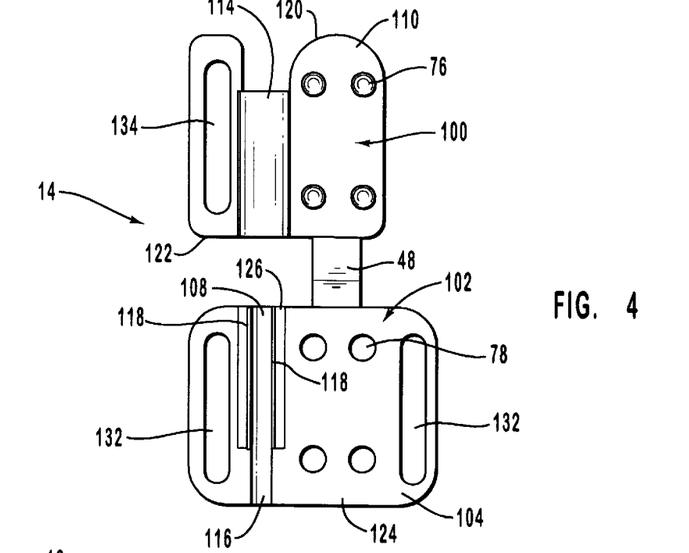
FIG. 4 is a top elevation view of the second holder illustrated in FIG. 1 as unassembled.
Figure 5:
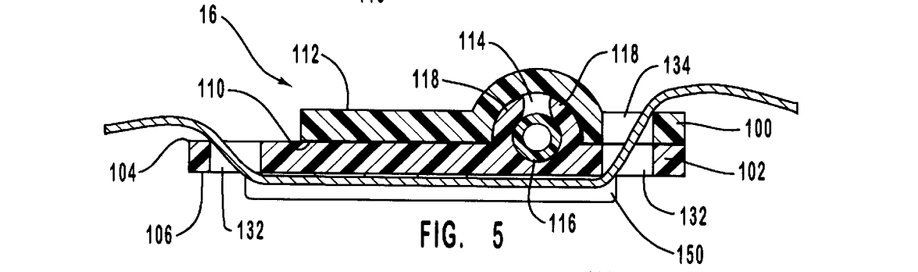
FIG. 5 is a partial cross-sectional elevation view taken along section line 5—5 in FIG. 1.

Second holder 16 is illustrated in FIGS. 4 and 5. Second holder 16 comprises a top portion 100 and bottom portion 102. Bottom portion 102 of second holder 16 has an interior surface 104 and an exterior surface 106 proximate to the limb of the patient, such as arm 32. Interior surface 104 of bottom portion 102 has a channel 108 formed therein.

Top portion 100 of second holder 16 has a interior surface 110 and exterior surface 112. Top portion 100 is securable to interior surface 104 of bottom portion 102 by flexible hinge 48. Interior surface 110 of top portion 100 has a recess 114 configured to cooperate with channel 108 on interior surface 104 of bottom portion 102. Recess 114 in interior surface 110 of top portion 100 and channel 108 in said bottom portion 102 define elongated hole 30.

Top portion 100 has a proximal side 120 and a distal side 122. Similarly, bottom portion 102 has a proximal side 124 and a distal side 126. As illustrated in FIG. 4, distal side 122 of top portion 100 is hingedly attached to distal side 126 of bottom portion 102 by flexible hinge 48. Other methods of connecting top portion 100 and bottom portion 102 are equally effective in carrying out the intended function thereof. In addition, other locations for flexible hinge 48 work equally as well. Top portion 100 and bottom portion 102 could be configured by way of example and not limitation, a string-like member, or have a continuous flexible hinge along an entire edge making top portion 100 and bottom portion 102 more of a one piece unit In addition, other locations for hinge 48 to attach top portion 100 and bottom portion 102 work equally as well. It can be appreciated that top portion 100 and bottom portion 102 are not required to be connected at all. Top portion 100 and bottom portion 102 could be two separate independent pieces and perform the function thereof equally effectively. In the preferred embodiment, top portion 100 is hingedly connected to bottom portion 102 for ease in assembly as well as manufacturing.

Channel 108 formed in bottom portion 102 of second holder 16 includes a recess 116 formed in interior surface 104 of bottom portion 102 and a pair of resilient substantially upwardly extending walls 118 extending substantially upward from interior surface 104 of bottom portion 102. Substantially upwardly extending walls 118 have a spaced apart relationship and recess 116 is between substantially upwardly extending walls 118.

Channel 108 has substantially the same configuration as channel 60 illustrated in FIG. 3A and is configured to compliment the size and shapes of various tubing used in medical procedures. The discussion relative to FIG. 3A is equally applicable to channel 108. The cross-section of channel 108 in a plane substantially perpendicular to interior surface 104 of bottom portion 102 is configured to receive flexible tubing 20. Channel 108 is conformable to flexible tubing 20 without exerting pressure on flexible tubing 20 when top portion 100 is selectively secured to bottom portion 102.

The cross-section of channel 108 is preferably substantially U-shaped or curvealinear and made to compliment the shape of tubing 20 in a plane substantially perpendicular to interior surface 104 of bottom portion 102. Like channel 60, in first holder 14 shown in FIG. 3A, the pair of substantially upwardly extending walls 118 in channel 108 are far enough apart that flexible tubing 20 can be disposed in channel 108 without substantially upwardly extending walls 118 exerting compressive force on tubing 20 when tubing 20 is disposed in channel 108. The pair of substantially upwardly extending walls 118 have a varying wall thickness to assist channel 108 to cooperate with recess 114 in top portion 100 to form elongated hole 30. FIG. 5 illustrates that resilient substantially upwardly extending walls 118 conform to recess 114 formed in top portion 100 of second holder 16 when top portion 100 is removably secured to bottom portion 102.

In an alternate embodiment of channel 108, the pair of substantially upwardly extending walls 118 are upright or substantially perpendicular to interior surface 104 of bottom portion 102. In this embodiment, channel 108 would still have a substantially U-shaped cross-section in a direction perpendicular to interior surface 104 of bottom portion 102.

Interior surface 110 of top portion 100 of second holder 16 is selectively and removably secured to interior surface 104 of bottom portion 102 of second holder 16 by male connectors 76 and female connectors 78. As illustrated in FIG. 4, male connectors 76 are formed on interior surface 110 of top portion 100 and extend outwardly from interior surface 110. Female connectors 78 are formed in bottom portion 102 and are configured to cooperate with male connectors 76 to selectively, nondestructively connect cover 100 to base 102. Male connectors 76 and female connectors 78 on second holder 16 may have alternate embodiments as previously discussed relative to first holder 14. Male connectors 76 and corresponding female connectors 78 are one possible embodiment of a structure capable of performing a function of a closing means for selectively, nondestructively connecting interior surface 110 of top portion 100 to interior surface 104 of bottom portion 102. By way of example and not limitation, other configurations of a closing means include top portion 100 is configured to snap fit over bottom portion 102 or a male member that can be press fit or snap fit into a recess configured to releasably cooperate with the male member.

Second holder 16 further includes elongated apertures 132 and 134 configured to receive second elongated strap 34. In one embodiment, illustrated in FIGS. 4 and 5, bottom portion 102 of second holder 16 has an elongated aperture 132 at each side. Top portion 100 of second holder 16 has a single elongated aperture 134 that is configured to be aligned with one of elongated apertures 132 in bottom portion 102 when top portion 100 is removably secured to bottom portion 102 by male connectors 76 and female connectors 78. Second elongated strap 34 is removably disposed through elongated apertures 132 in bottom portion 100 as well as elongated aperture 134 in top portion 100. Second elongated strap 134 passes through one elongated aperture 132 in bottom portion 102 and aligned elongated aperture 134 in top portion 100 that are both on one side of second holder 16 to prevent top portion 100 from accidentally opening and freeing flexible tubing 20. Second elongated strap is then removably disposed in the remaining elongated aperture 132.

Similar to first elongated strap 22, second elongated strap 34 has hook-and-pile fasteners 24 attached to second elongated strap 34 for selectively, nondestructively fixing second elongated strap 34 in place around the limb of the patient without direct adhesion to the skin of the patient. Second elongated strap 34 is one possible embodiment of structure performing the function of a second attaching means for securing second holder 16 in place on a limb of the patient.

Second holder 16 is one example of structure capable of performing the function of a second holding means for anchoring flexible tubing 20 on a patient at a location remote from the first holding means.

As shown in FIGS. 3 and 5, first holder 14 and second holder 16 may have outwardly extending generally elongated ridges 150 to keep first and second holders 14 and 16, respectively, in contact with the skin of the patient. Bottom surface 56 of base 50 has ridge 150 formed along proximal side 58 and distal side 57 of base 50. Similarly, second holder 16 has ridges 150 formed along proximal side 124 and distal side 126 of bottom portion 102 that extend outwardly from exterior surface 106 of bottom portion 102.

In the embodiments illustrated in FIGS. 3 and 5, ridges 150 are generally perpendicular to the limb of the patient and are meant to contact the skin of the patient and increase the friction between the skin and ridge 150 to prevent unintentional movement of first holder 14 or second holder 16 without causing abrasion to or bruising of the skin of the patient. Ridges 150 engage the skin on the limb of the patient and prevent movement of first holder 14 and second holder 16 along the longitudinal length of the limb of the patient. Ridges 150 are an example of structure capable of performing the function of a friction means for frictionally engaging the skin of the patient to keep first holder 14 and second holder 16 in place along the longitudinal axis of the limb of the patient.

The preferred material that first holder 14 and second holder 16 may be substantially composed of are selected from the group comprising polyurethane, polypropylene, or other flexible resilient polymers. In one preferred embodiment, first holder 14 and second holder 16 substantially comprise polyurethane. First holder 14 and second holder 16 are made of a flexible, resilient material that has a durometer reading in the range of about 75 A to about 55 D. First holder 14 and second holder 16 are preferably substantially translucent or transparent.

To use tapeless anchoring system 10 after a skin penetrating instrument, such as an intravenous needle 18, has been securely inserted into the limb of the patient, flexible hollow tubing 20 is formed into a loop while ensuring that sufficient slack for movement of the limb is provided. When first holder 14 is unassembled, as illustrated in FIG. 2, the loop of flexible tubing 20 is disposed into conformable channel 60 in base 50. While the loop of flexible tubing 20 is disposed in channel 60, compressive force is not exerted upon flexible tubing 20 and the flow of fluid through flexible tubing 20 is not reduced. Cover 52 of first holder 14 is then closed over flexible tubing 20 and is selectively, nondestructively secured to top surface 54 of base 50 by male connectors 76 and female connectors 78.

After flexible tubing 20 is enclosed in passageway 28, first elongated strap 34 is disposed through elongated apertures 132 with first elongated strap 34 going across exterior surface 106 between elongated apertures 132. Preferably, first elongated strap 34 is disposed in elongated apertures 132 in base 50 prior to positioning flexible tubing 20 in channel 60. First elongated strap 34 is then wrapped around the limb of the patient and selectively secured in place on the patient by hook-and-pile fastener 24 without direct adhesion to the skin of the patient.

Elongated flexible tubing 22 is then extended along the limb of the patient usually in a direction parallel to the skin piercing instrument 18 as illustrated in FIG. 1. With second holder 16 in an unassembled position as illustrated in FIG. 4, flexible tubing 20 is then disposed in channel 108 in bottom portion 102. Like channel 60 in first holder 14, conformable channel 108 does not compress or reduce the fluid flow through flexible tubing 20.

Top portion 100 of second holder 16 is then selectively and removably securable to bottom portion 102 of second holder 16 by male connectors 76 and corresponding female connectors 78. After enclosing flexible tubing 20 in elongated hole 30, second elongated strap 34 is then attached to second holder 16.

In one embodiment illustrated in FIG. 4, second elongated strap 34 must be attached after top portion 100 has been removably secured to bottom portion 102 of second holder because second elongated strap 34 is disposed through both elongated apertures 132 and 134 on one side of second holder 16 and then is also disposed in elongated aperture 132 of bottom portion 102 of second holder 16. Having elongated aperture 134 formed in the top portion of second holder 16 prevents the accidental opening of top portion 100 and bottom portion 102, particularly by flexible tubing 20 being caught upon an object or person. Second elongated strap 34 extends across exterior surface 106 of bottom portion 102 between elongated apertures 132.

Hook-and-pile fastener 24 attached to second elongated strap 34 is the same as that used with first elongated strap 22. Hook-and-pile fastener 24 on second elongated strap 34 enables second elongated strap 34 to be wrapped around the limb of the patient to selectively secure the second holder 16 in place on the patient without direct adhesion to the skin of the patient.

Figure 6:
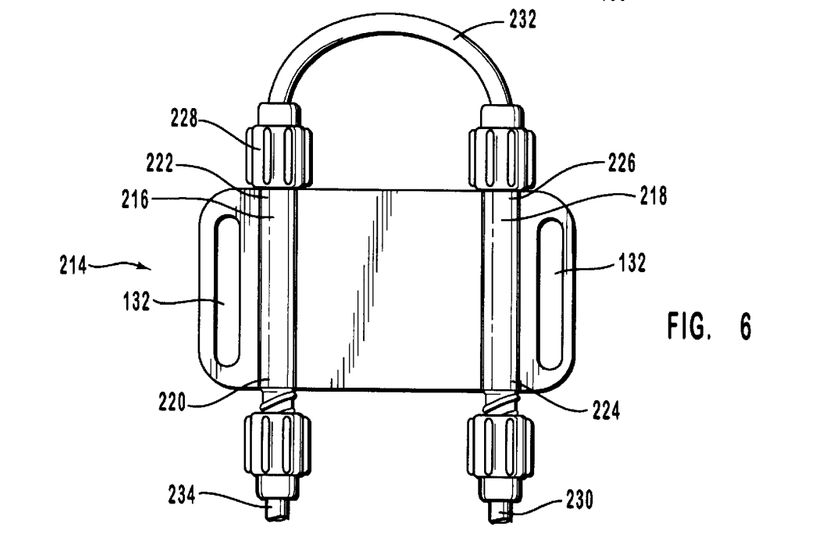
FIG. 6 is a top elevation view of a second embodiment of the first holder.

FIG. 6 illustrates an alternate embodiment of first holder 14. FIG. 6 shows a one-piece embodiment of first holder 214 that has two tubular passageways 216 and 218 extending completely through first holder 214. Tubular passageway 216 has a first end 220 and a second end 222. Similarly, tubular passageway 218 has a first end 224 and a second end 226.

A connector 228 is attached to each end of tubular passageways 216 and 218 to connect flexible tubing to first holder 214 to form a fluid pathway. Connectors 228 may be connectors that are commonly used in the medical field such as male and female Luer connectors. Connectors 228 are one embodiment of structure capable of performing the function of a coupling means for releasably connecting tubing to passageways 216 and 218 formed in first holder 214.

A skin penetrating instrument such as a needle 18 (FIG. 1) is attached to hollow tubing. A first piece of flexible tubing 230 is attached to connector 228 at first end 224 of tubular passageway 218. A second piece of tubing 232 is attached to connectors 228 at second end 226 of tubular passageway 218 and second end 222 of tubular passageway 216. In this embodiment, as illustrated in FIG. 6, second piece of tubing 232 is curved. To protect second piece of tubing 232 from being totally or partially occluded, second piece of tubing 232 preferably comprises a less flexible material that is capable of preventing distortion and potential pinching of the second piece of tubing 232.

A third piece of flexible tubing 234 is attached to connector 228 at first end 220 of tubular passageway 216 and extends up the limb of the patient to the fluid source. As can be seen from FIG. 6, tubular passageways 216 and 218 are in fluid communication. Fluid flows from first piece of tubing 230 through tubular passageway 218 to second piece of tubing 232. Fluid then flow through second piece of tubing 232 to tubular passageway 216 until it reaches third piece of tubing 234 which leads to the fluid source. Of course the fluid can flow in the reverse direction. First holder 214 also includes elongated apertures 132 configured to receive first elongated strap 34.

It can be appreciated that first holder 214 may have only one passageway formed therein, for example and not limitation, in the shape of passageway 28 illustrated in FIG. 1. In the case of a single curved passageway formed in first holder 214, second piece of tubing 232 would not be necessary. With this embodiment, first piece of tubing 230 is in fluid communication with third piece of tubing 234.

To use tapeless the alternate embodiment of first holder first piece of hollow tubing 230 is attached to connector 228 at first end 224 of tubular passageway 218. First piece of tubing 230 has a cooperating connector attached to the end remote from the skin penetrating instrument 18 (FIG. 1) so as to be able to be removably coupled with connector 228. Sufficient slack for movement of the limb is provided.

Second piece of tubing 232 is attached to connector 228 at second end 226 of tubular passageway 218 and second end 222 of tubular passageway 216. Second piece of tubing 232 has a connector attached to each end configured to removably couple with connectors 228 attached to first holder 214. Second piece of tubing 232 may be flexible tubing or may be less flexible and preformed into a desired configuration.

A third piece of tubing 234 is attached to connector 228 at first end 220 of tubular passageway 216. Third piece of tubing 234 is in fluid communication with a fluid source. Third piece of tubing 234 has a connector attached to one end for being removably connected with connector 228 at first end 220 of tubular passageway 216.

Once the pieces of tubing are all connected to first connector 214 the skin penetrating instrument such as needle 18 illustrated in FIG. 1 is in fluid communication with the fluid source. Needle 18 is now securely inserted into the limb of the patient. After fluid communication has been established between the fluid source and skin penetrating instrument, first elongated strap 34, shown in FIG. 1, is disposed through elongated apertures 132 with first elongated strap 34 going across exterior surface 106 between elongated apertures 132. First elongated strap 34 is then wrapped around the limb of the patient and selectively secured in place on the patient by hook-and-pile fastener 24 without direct adhesion to the skin of the patient. It can be appreciated that alternate configurations of passageways 216 and 218 perform the function thereof equally effectively. In addition, instead of two passageways 216 and 218, and alternate embodiment may have one passageway in fluid communication with the skin penetrating needle 18 (FIG. 1) performs the function thereof equally effectively.

Elongated third piece of tubing 234 is then extended along the limb of the patient usually in a direction parallel to the skin piercing instrument 18 as illustrated in FIG. 1. A second holder, such as second holder 16, may be used with first holder 214. With second holder 16 in an unassembled position as illustrated in FIG. 4, third piece of tubing 234 is then disposed in channel 108 in bottom portion 102. Conformable channel 108 comprises a pair of substantially upwardly extending walls 118 that do not compress or reduce the fluid flow through third piece of tubing 234.

Top portion 100 of second holder 16 is then selectively and removably securable to bottom portion 102 of second holder 16 by male connectors 76 and corresponding female connectors 78. After enclosing third piece of tubing 234 in elongated hole 30, second elongated strap 34 is then attached to second holder 16.

In one embodiment illustrated in FIG. 4, second elongated strap 34 must be attached after top portion 100 has been removably secured to bottom portion 102 of second holder because second elongated strap 34 is disposed through both elongated apertures 132 and 134 on one side of second holder 16 and then is also disposed in elongated aperture 132 of bottom portion 102 of second holder 16. Having elongated aperture 134 formed in the top portion of second holder 16 prevents the accidental opening of top portion 100 and bottom portion 102, particularly by third piece of tubing 234 being caught upon an object or person. Second elongated strap 34 extends across exterior surface 106 of bottom portion 102 between elongated apertures 132.

Hook-and-pile fastener 24 attached to second elongated strap 34 is the same as that used with first elongated strap 22. Hook-and-pile fastener 24 on second elongated strap 34 enables second elongated strap 34 to be wrapped around the limb of the patient to selectively secure the second holder 16 in place on the patient without direct adhesion to the skin of the patient.

The invention may be embodied in other specific forms without parting from its spirit or essential characteristics. The described embodiments are to be considered in all respects as only illustrative and not restrictive. The scope of the invention is therefore, indicated by the appended claims rather than by the foregoing description. All changes that come within the meaning and range of equivalency of the claims are to be embraced within the scope thereof.

What is claimed is:

1. A tapeless anchoring system comprising:
    (a) first holding means for anchoring hollow tubing in a substantially fixed position on a patient, said first holding means having a passageway formed therein configured to cooperate with said tubing without exerting compressive force thereon and without reducing the flow of fluid through said tubing, said passageway being configured to enclose said tubing therein, said first holding means comprising:
        (i) a base having a top surface and a bottom surface proximate to said patient, said top surface of said base having a conformable channel formed therein configured to receive a portion of said tubing, said base having a proximal side and a distal side, said channel including:
            a second recess formed in said top surface of said base; and
            a pair of resilient substantially upwardly extending walls projecting substantially upward from said top surface of said base, said pair of substantially upwardly extending walls having a spaced apart relationship with said second recess therebetween; and
        (ii) a cover securable to said top surface of said base, said cover having a top surface and a bottom surface configured to cooperate with said channel in said top surface of said base to form said passageway, said cover having a proximal side and a distal side; and
    (b) first attaching means for securing said first holding means in place on said patient.

2. A tapeless anchoring system as recited in claim 1, wherein said bottom surface of said cover has a first recess formed therein, said first recess in said cover and said channel in said base defining said passageway.

3. A tapeless anchoring system as recited in claim 1, wherein said channel formed in said top surface of said base and said first recess formed in said bottom surface of said cover are substantially curvealinear in a plane parallel with said top surface of said base.

4. A tapeless anchoring system as recited in claim 1, wherein:
    (a) said channel formed in said top surface of said base has a tapered third recess at one end that widens toward proximal side of said base; and
    (b) said first recess formed in said bottom surface of said cover has a corresponding tapered fourth recess configured to cooperate with said third recess, thereby enabling a connector attached to said tubing to be disposed between said tapered third recess and said tapered fourth recess.

5. A tapeless anchoring system as recited in claim 1, wherein:
    (a) said channel formed in said top surface of said base has an enlarged third recess at one end; and
    (b) said first recess formed in said bottom surface of said cover has a corresponding enlarged fourth recess configured to cooperate with said enlarged third recess formed in said top surface of said base, thereby enabling a connector to be disposed therein proximate to said channel.

6. A tapeless anchoring system as recited in claim 1, wherein said base and said cover are hingedly connected.

7. A tapeless anchoring system as recited in claim 1, wherein said first attaching means comprises:
    (a) an elongated strap attached to said first holding means, said strap being configured to be wrapped around the limb of said patient to secure said first holding means in place on said patient; and
    (b) fastening means, attached to said strap, for selectively, nondestructively fixing said strap in place around the limb of said patient.

8. A tapeless anchoring system as recited in claim 7, wherein said fastening means comprise hook and pile fasteners.

9. A tapeless anchoring system comprising:
    (a) first holding means for anchoring hollow tubing in a substantially fixed position on a patient, said first holding means having a passageway formed therein configured to removably receive a portion of said tubing without exerting compressive force thereon and without reducing the flow of fluid through said tubing, said first holding means comprising:
        (i) a base having a top surface and a bottom surface proximate to said patient, said top surface of said base having a conformable channel formed therein configured to receive a portion of tubing, said base having a proximal side and a distal side, said channel including:

a second recess formed in said top surface of said base; and a pair of resilient substantially upwardly extending walls projecting substantially upward from said top surface of said base, said pair of substantially upwardly extending walls having a spaced apart relationship with said second recess therebetween; and (ii) a cover securable to said top surface of said base, said cover comprising a top surface and a bottom surface, said bottom surface of said cover has a first recess formed therein configured to cooperate with said channel in said top surface of said base to form said passageway, said cover having a proximal side and a distal side;

(b) second holding means for anchoring said tubing on said patient at a location remote from said first holding means, said second holding means having an elongated hole formed therethrough configured to removably receive said tubing therein;

(c) first attaching means for securing said first holding means in place on said patient; and (d) second attaching means for securing said second holding means in place on said patient.

10. A tapeless anchoring system as recited in claim 9, wherein said tubing is removably disposed in said elongated hole in said second holding means without compressive force being exerted on said tubing and without the flow of fluid through said tubing being reduced.

11. A tapeless anchoring system as recited in claim 9, wherein said channel in said top surface of said base has a substantially U-shaped cross-section in a plane generally perpendicular to said top surface of said base.

12. A tapeless anchoring system as recited in claim 9, wherein said first holding means further comprises first closing means for selectively, nondestructively connecting said top surface of said base to said bottom surface of said cover.

13. A tapeless anchoring system as recited in claim 12, wherein said first closing means comprise:

(a) a plurality of outwardly extending male connectors; and (b) a plurality of female connectors configured to cooperate with said male connectors to selectively, nondestructively secure said cover to said base of said first holding means.

14. A tapeless anchoring system as recited in claim 9, wherein said first attaching means comprises:

(a) a first elongated strap connected to said first holding means, said first strap being configured to be wrapped around the limb of said patient to secure said first holding means in place on said patient; and (b) fastening means, attached to said first strap, for selectively, nondestructively fixing said strap in place around the limb of said patient.

15. A tapeless anchoring system as recited in claim 14, wherein said fastening means on said first strap comprises hook and pile fasteners.

16. A tapeless anchoring system as recited in claim 9, wherein said second holding means further comprises second closing means for selectively, nondestructively connecting said interior surface of said bottom portion to said interior surface of said top portion.

17. A tapeless anchoring system as recited in claim 16, wherein said second closing means comprises:

(a) a plurality of outwardly extending male connectors; and (b) a plurality of female connectors configured to removably cooperate with said male connectors to selectively nondestructively connect said top portion to said bottom portion.

18. A tapeless anchoring systems as recited in claim 9, wherein said second attaching means comprises:

(a) a second elongated strap connected to said second holding means, said second strap being configured to be wrapped around the limb of said patient to secure said second holding means in place on said patient;

(b) fastening means, attached to said second strap, for selectively, nondestructively fixing said strap emplace around the limb of said patient.

19. A tapeless anchoring system as recited in claim 18, wherein said fastening means of said second strap comprises hook and pile fasteners.

20. A tapeless anchoring system as recited in claim 9, wherein said first holder is substantially composed of materials selected from the group consisting of polyurethane, polypropylene, and other resilient polymers.

21. A tapeless anchoring system comprising:

(a) a first holder having a passageway formed therein configured to removably enclose a portion of tubing, said first holder comprising:

(i) a base comprising a top surface and a bottom surface, said top surface of said base having a channel formed therein configured to receive a portion of said tubing therein; and (ii) a cover securable to said top surface of said base, said cover comprising a top surface and a bottom surface, said bottom surface having a first recess formed therein configured to cooperate with said channel to form said passageway;

(b) a second holder remotely positioned from said first holder, said second holder having an elongated hole formed therein configured to removably receive a portion of said tubing, said second holder comprising:

(i) a bottom portion proximate comprising an interior surface and an exterior surface, said interior surface of said bottom portion having a channel formed therein; and (ii) a top portion securable to said interior surface of said bottom portion, said top portion comprising an exterior surface and an interior surface, said interior surface having a recess formed therein configured to cooperate with said channel in said interior surface of said bottom portion to form said elongated hole;

(c) a first elongated strap connected to said first holder, said first elongated strap being configured to be wrapped around the limb of a patient to selectively, nondestructively secure said first holder in place on said patient without direct adhesion to the skin of said patient; and (d) a second elongated strap connected to said second holder, said second elongated strap being configured to be wrapped around the limb of said patient to selectively, nondestructively secure said second holder in place on said patient without direct adhesion to the skin of said patient.

22. A tapeless anchoring system as recited in claim 21, wherein said passageway is substantially curvealinear in a plane parallel to said top surface of said base.

23. A tapeless anchoring system as recited in claim 21, further comprising hook and pile fasteners attached to said first and second elongated straps for selectively, nondestructively securing said first and second holder in place on said patient.

24. A tapeless anchoring system as recited in claim 21, further comprising friction means for keeping said first and second holders in place against the skin of the patient.

25. A tapeless anchoring system as recited in claim 24, wherein said friction means comprises an outwardly extending ridge configured to contact the skin of the patient.

26. A tapeless anchoring system as recited in claim 21, wherein said attaching means further comprises an aperture formed in said base of said first holder configured to receive said first strap therethrough.

27. A tapeless anchoring system as recited in claim 21, wherein said attaching means further comprises an aperture formed in said bottom portion of said second holder configured to receive said second strap therethrough.

28. A tapeless anchoring system as recited in claim 21, wherein said first holder and said second holder are substantially composed of polypropylene.

29. A tapeless anchoring system as recited in claim 21, wherein said first holder and said second holder are substantially translucent or transparent.

30. A tapeless anchoring system comprising:
  (a) a first holder comprising a passageway formed therein in fluid communication with a skin penetrating instrument on a patient, said passageway having a first end and a second end;
  (b) a second holder remotely positioned from said first holder, said second holder having an elongated hole formed therein configured to removably receive a portion of said tubing, said second holder comprising:
    (i) a bottom portion proximate comprising an interior surface and an exterior surface, said interior surface of said bottom portion having a channel formed therein; and
    (ii) a top portion securable to said interior surface of said bottom portion, said top portion comprising an exterior surface and an interior surface, said interior surface having a recess formed therein configured to cooperate with said channel in said interior surface of said bottom portion to form said elongated hole;
  (c) a first elongated strap connected to said first holder, said first elongated strap being configured to be wrapped around the limb of a patient to selectively, nondestructively secure said first holder in place on said patient without direct adhesion to the skin of said patient; and
  (d) a second elongated strap connected to said second holder, said second elongated strap being configured to be wrapped around the limb of said patient to selectively, nondestructively secure said second holder in place on said patient without direct adhesion to the skin of said patient.

31. A tapeless anchoring system, as recited in claim 30, further comprising:
  (a) hollow tubing releasably connected to said passageway in said first holder; and
  (b) coupling means, attached to said passageway in said first holder, for releasably attaching said hollow tubing to said passageway in said first holder.

32. A tapeless anchoring system comprising:
  (a) first holding means for anchoring hollow tubing in a substantially fixed position on a patient, said first holding means having a passageway formed therein configured to removably receive a portion of said tubing without exerting compressive force thereon and without reducing the flow of fluid through said tubing;
  (b) second holding means for anchoring said tubing on said patient at a location remote from said first holding means, said second holding means having an elongated hole formed therethrough configured to removably receive said tubing therein, said second holding means comprising:
    (i) a bottom portion proximate to said patient, said bottom portion comprising a interior surface and an exterior surface proximate to said patient, said interior surface of said bottom portion having a conformable channel formed therein; and
    (ii) an top portion removably attached to interior surface of said bottom portion, said top portion having an exterior surface and an interior surface configured to cooperate with said channel in said interior surface of said bottom portion to form said elongated hole;
  (c) first attaching means for securing said first holding means in place on said patient; and
  (d) second attaching means for securing said second holding means in place on said patient.

33. A tapeless anchoring system as recited in claim 32, wherein said interior surface of said top portion has a first recess formed therein, said first recess in said top portion and said channel in said bottom portion defining said elongated hole.

34. A tapeless anchoring system as recited in claim 32, wherein said channel in said interior surface of said bottom portion comprises:
  (a) a second recess formed in said interior surface of said bottom portion; and
  (b) a pair of resilient substantially upwardly extending walls projecting substantially upward from said interior surface of said bottom portion, said pair of substantially upwardly extending walls having a spaced apart relationship with said second recess therebetween.

35. A tapeless anchoring system as recited in claim 34, wherein said channel in said interior surface of said bottom portion has a substantially U-shaped cross-section in a plane generally perpendicular to said interior surface of said bottom portion.

36. A tapeless anchoring system as recited in claim 32, wherein said top portion and said bottom portion of said second holding means are hingedly attached.

37. A tapeless anchoring system as recited in claim 32, wherein said second holder is substantially composed of materials selected from the group consisting of polyurethane, polypropylene, and other resilient polymers.

* * * * *